US010695508B2

(12) United States Patent
Lorberbaum et al.

(10) Patent No.: US 10,695,508 B2
(45) Date of Patent: Jun. 30, 2020

(54) REDUCING PAIN OF SKIN PIERCING USING VIBRATION

(71) Applicant: BING INNOVATIONS, LLC, Boca Raton, FL (US)

(72) Inventors: Mark Lorberbaum, Boca Raton, FL (US); Philip Ralabate, Boca Raton, FL (US); Paul Dicesare, Boca Raton, FL (US)

(73) Assignee: BING INNOVATIONS, LLC, Boca Raton, FL (US)

( * ) Notice: Subject to any disclaimer, the term of this patent is extended or adjusted under 35 U.S.C. 154(b) by 285 days.

(21) Appl. No.: 15/571,211

(22) PCT Filed: Apr. 29, 2016

(86) PCT No.: PCT/US2016/029971
§ 371 (c)(1),
(2) Date: Nov. 1, 2017

(87) PCT Pub. No.: WO2016/178952
PCT Pub. Date: Nov. 10, 2016

(65) Prior Publication Data
US 2018/0264205 A1 Sep. 20, 2018

Related U.S. Application Data

(63) Continuation-in-part of application No. 14/803,535, filed on Jul. 20, 2015, now Pat. No. 9,463,287.
(Continued)

(51) Int. Cl.
A61M 5/42 (2006.01)
A61M 37/00 (2006.01)
(Continued)

(52) U.S. Cl.
CPC ........ A61M 5/422 (2013.01); A61M 37/0076 (2013.01); A61B 18/20 (2013.01);
(Continued)

(58) Field of Classification Search
CPC ..................... A61H 1/00; A61H 13/00; A61H 23/02–2023/029; A61H 39/007;
(Continued)

(56) References Cited

U.S. PATENT DOCUMENTS 1,485,963 A 3/1924 Curry
2,247,258 A 6/1941 Shepard
(Continued)

FOREIGN PATENT DOCUMENTS

AU 2010229783 9/2015
CA 2756890 9/2010
(Continued)

OTHER PUBLICATIONS

Notice of Allowance for Canadian Application No. 2,756,890 dated Aug. 2, 2017.
(Continued)

Primary Examiner — Valerie L Woodward
(74) Attorney, Agent, or Firm — Paul D. Bianco; Gary S. Winer; Fleit Intellectual Property Law

(57) ABSTRACT

An instrument is applied to body tissue of a body part to produce vibration to thereby reduce pain of injection or other pain producing stimulus. The device has a frame, and a source of vibration connected to the frame. A removable tip is connectable to the frame which has a distal end that is connected to the source of vibration when the tip is connected to the frame, to thereby vibrate the distal end when the source of vibration is activated. At the distal end of the tip are mutually facing arms which define an opening between them. Each arm forms a projection which extends
(Continued)

at an angle from the arm. The projections are shaped to fit the body part so that the arms and projections are sized and dimensioned to position, retain, and transmit vibration to the body part in a position proximate the opening.

25 Claims, 8 Drawing Sheets

Related U.S. Application Data

(60) Provisional application No. 62/208,860, filed on Aug. 24, 2015, provisional application No. 62/155,769, filed on May 1, 2015.

(51) Int. Cl.

| | | |
|---|---|---|
| *A61H 23/02* | (2006.01) | |
| *A61B 18/00* | (2006.01) | |
| *A61B 90/00* | (2016.01) | |
| *A61B 90/98* | (2016.01) | |
| *A61B 18/20* | (2006.01) | |
| *A61B 90/50* | (2016.01) | |
| *A61B 17/00* | (2006.01) | |

(52) U.S. Cl.
CPC ............. *A61B 90/50* (2016.02); *A61B 90/98* (2016.02); *A61B 2017/00734* (2013.01); *A61B 2018/00452* (2013.01); *A61B 2090/0803* (2016.02); *A61H 23/02* (2013.01); *A61H 2201/013* (2013.01); *A61H 2205/067* (2013.01)

(58) Field of Classification Search
CPC ...... A61H 39/08–086; A61H 2201/013; A61H 2205/067; A61M 5/42; A61M 5/422; A61M 5/427; A61M 37/0076; A61M 37/0092; F16M 11/00; F16M 11/04; F16M 11/041
See application file for complete search history.

(56) References Cited

U.S. PATENT DOCUMENTS

| | | | |
|---|---|---|---|
| 2,258,857 A | 10/1941 | McCann | |
| 2,574,945 A | 11/1951 | Werner | |
| 3,590,232 A | 6/1971 | Sadowski | |
| 3,620,209 A | 11/1971 | Kravitz | |
| 3,837,595 A | 9/1974 | Boone | |
| 4,091,805 A | 5/1978 | Clark | |
| 4,572,180 A | 2/1986 | Deenadayalu | |
| 4,593,973 A | 6/1986 | Yoshida | |
| 4,785,796 A | 11/1988 | Mattson | |
| 4,867,141 A | 9/1989 | Nakada et al. | |
| 5,437,606 A | 8/1995 | Tsukamoto | |
| 5,542,845 A | 8/1996 | Jenkins | |
| 5,611,771 A | 3/1997 | Taylor | |
| 5,636,988 A | 6/1997 | Murayama | |
| 5,639,238 A | 6/1997 | Fishburne, Jr. | |
| 5,647,851 A | 7/1997 | Pokras | |
| 5,647,853 A | 7/1997 | Feldmann et al. | |
| 5,692,900 A | 12/1997 | Fischer | |
| 5,704,902 A | 1/1998 | Vandenbelt et al. | |
| 5,928,170 A | 7/1999 | Garrigan | |
| 5,938,435 A | 8/1999 | Raspino | |
| 5,989,022 A | 11/1999 | Yamamoto | |
| 6,030,210 A | 2/2000 | Bianchetti | |
| 6,355,007 B1 | 3/2002 | Zuckerbrod | |
| 6,436,035 B1 | 8/2002 | Toth et al. | |
| 6,602,229 B2 | 8/2003 | Coss | |
| 6,923,762 B1 | 8/2005 | Creaghan, Jr. | |
| 7,244,266 B2 | 7/2007 | Garthe | |
| 7,981,071 B2 | 7/2011 | Goldberg | |
| 8,121,696 B2 | 2/2012 | Vallero | |
| 8,622,952 B2 | 1/2014 | Goldberg | |
| 8,668,664 B2 | 3/2014 | Goldberg | |
| 8,690,872 B2 | 4/2014 | Jayaraj | |
| 8,777,897 B2 | 7/2014 | Butterfield | |
| 9,168,340 B2 | 10/2015 | Goldberg et al. | |
| 9,200,667 B1 | 12/2015 | Hsu | |
| 9,463,287 B1 | 10/2016 | Lorberbaum et al. | |
| 9,539,171 B2 | 1/2017 | Goldberg et al. | |
| 9,675,766 B2 | 6/2017 | Goldberg et al. | |
| 9,732,785 B2 | 8/2017 | Kobayashi | |
| 2002/0082564 A1 | 6/2002 | Pham | |
| 2003/0040714 A1 | 2/2003 | Coss | |
| 2003/0195644 A1 | 10/2003 | Borders et al. | |
| 2003/0225429 A1 | 12/2003 | Garthe et al. | |
| 2004/0077977 A1 | 4/2004 | Ella | |
| 2004/0254599 A1 | 12/2004 | Lipoma et al. | |
| 2005/0215952 A1 | 9/2005 | Brunel | |
| 2006/0106363 A1 | 5/2006 | Aravena et al. | |
| 2007/0088245 A1 | 4/2007 | Babaev et al. | |
| 2007/0145155 A1 | 6/2007 | Scarlatella | |
| 2007/0150004 A1 | 6/2007 | Colloca et al. | |
| 2007/0156179 A1 | 7/2007 | Karashurov | |
| 2007/0167943 A1 | 7/2007 | Janssen et al. | |
| 2008/0017764 A1* | 1/2008 | Nan | A61H 19/44 248/133 |
| 2008/0086159 A1 | 4/2008 | Zweifler | |
| 2008/0215039 A1 | 4/2008 | Slatkine | |
| 2008/0195006 A1 | 8/2008 | Stark et al. | |
| 2008/0255483 A1* | 10/2008 | Goldberg | A61H 7/005 601/72 |
| 2009/0047624 A1 | 2/2009 | Tsai | |
| 2009/0108153 A1 | 4/2009 | Hung | |
| 2009/0281464 A1 | 11/2009 | Cioanta et al. | |
| 2010/0125172 A1 | 5/2010 | Jayaraj | |
| 2010/0179457 A1* | 7/2010 | Blaine | A61H 23/0263 601/46 |
| 2011/0054386 A1 | 3/2011 | Blaine et al. | |
| 2011/0270154 A1 | 11/2011 | Goldberg | |
| 2011/0319812 A1* | 12/2011 | Goldberg | A61M 5/422 604/22 |
| 2012/0016292 A1* | 1/2012 | Goldberg | A61H 7/005 604/22 |
| 2012/0029422 A1 | 2/2012 | Goldberg | |
| 2012/0070799 A1* | 3/2012 | Metcalf | A61C 1/081 433/118 |
| 2013/0095508 A1 | 4/2013 | Campitelli et al. | |
| 2013/0197317 A1 | 8/2013 | Daniel et al. | |
| 2013/0204202 A1 | 8/2013 | Trombly et al. | |
| 2013/0317314 A1 | 11/2013 | Lampson | |
| 2014/0055588 A1 | 2/2014 | Bangera et al. | |
| 2014/0121557 A1 | 5/2014 | Gannon | |
| 2014/0131412 A1 | 5/2014 | Canton | |
| 2014/0187870 A1 | 7/2014 | Weber | |
| 2014/0188095 A1 | 7/2014 | Weber | |
| 2014/0188107 A1 | 7/2014 | Weber | |
| 2014/0188128 A1 | 7/2014 | Weber | |
| 2014/0316310 A1* | 10/2014 | Ackermann | A61N 1/36046 601/46 |
| 2014/0343432 A1 | 11/2014 | Humayun | |
| 2014/0371542 A1 | 12/2014 | Goldberg et al. | |
| 2014/0378940 A1 | 12/2014 | Lee | |
| 2015/0121557 A1 | 4/2015 | Pierce | |
| 2015/0134358 A1 | 5/2015 | Fisher | |
| 2015/0136922 A1 | 5/2015 | Shamsadov | |
| 2015/0186702 A1 | 7/2015 | Pletcher et al. | |
| 2015/0216618 A1 | 8/2015 | Jayaraj | |
| 2015/0306286 A1 | 10/2015 | Ross et al. | |
| 2017/0021113 A1 | 1/2017 | Goldberg | |
| 2018/0264205 A1 | 9/2018 | Bing | |

FOREIGN PATENT DOCUMENTS

| | | |
|---|---|---|
| CA | 2580792 | 10/2013 |
| CN | 102473201 A | 5/2012 |
| CN | 103826686 | 5/2014 |
| CN | 103826686 A | 5/2014 |
| CN | ZL201080016524.X | 8/2014 |
| EP | 2411074 | 2/2012 |
| FR | 2699083 A1 | 6/1994 |

(56) References Cited

FOREIGN PATENT DOCUMENTS

| | | |
|---|---|---|
| IL | 215355 | 9/2015 |
| JP | S6154832 | 4/1986 |
| JP | 548916 | 6/1993 |
| JP | 2002224183 | 8/2002 |
| JP | 2004129914 | 4/2004 |
| JP | 5549987 | 5/2014 |
| KR | 2012/0124742 | 11/2012 |
| RU | 2011141339 | 5/2013 |
| RU | 2523203 | 5/2014 |
| SU | 728859 A1 | 4/1980 |
| WO | 03024513 A1 | 3/2003 |
| WO | 2004000196 A1 | 12/2003 |
| WO | 2006/034324 | 3/2006 |
| WO | 2008/042936 | 4/2008 |
| WO | 2010/110823 | 9/2010 |
| WO | 2010/111611 | 9/2010 |
| WO | 2011005634 A1 | 1/2011 |
| WO | 2012/0163411 A1 | 12/2012 |
| WO | 2013/036625 | 3/2013 |
| WO | 2013036507 A1 | 3/2013 |
| WO | 2014/011740 A1 | 1/2014 |
| WO | 2015/081181 | 6/2015 |
| WO | 2016/178952 A1 | 11/2016 |

OTHER PUBLICATIONS

Notice of Allowance dated Oct. 21, 2013 for U.S. Appl. No. 13/179,674, filed Jul. 11, 2011.
Office Action dated Oct. 14, 2016 for Canadian Patent Application No. 2756890.
Office Action dated Jan. 15, 2016 for Canadian Patent Application No. 2756890.
Notice of Allowance dated Feb. 6, 2017 for U.S. Appl. No. 14/343,085.
Response to Office Action for U.S. Appl. No. 14/343,085, filed Nov. 14, 2016.
Supplemental Response filed Oct. 10, 2013 for U.S. Appl. No. 13/179,674.
International Search Report, dated Apr. 11, 2019, for PCT/US19/015360, filed Jan. 28, 2019.
International Search Report, Written Opinion dated Nov. 30, 2012 for PCT/US12/53744.
International Search Report and Written Opinion for PCT/US16/29971 filed Nov. 10, 2016.
Columbian Request for Technical Information dated Apr. 12, 2013 for application No. 11-140634.
Response to Columbian Request for Technical Information dated Jul. 15, 2013 for application No. 11-140634.
English translation of Japanese Office Action dated Jan. 7, 2014 for Japanese Patent Application No. JP2012-502291 filed on Sep. 20, 2012.
European Search Report (ESR) for EP application No. 107569266.1—PCT/US2010028858 dated Aug. 20, 2013.
For U.S. Appl. No. 13/253,572 Office Actions dated Sep. 17, 2013; Feb. 6, 2014 Responses filed Dec. 17, 2103; May 5, 2014.
Response dated Mar. 24, 2014 to Japanese Office Action for Application No. JP2012-502291 filed Sep. 20, 2012.
Office Action Summary dated Dec. 18, 2013 for MX/a/2011/010069.
International Search Report dated Dec. 13, 2012 for International Patent Application No. PCT/US2012/053943 filed Sep. 6, 2012.
International Preliminary Report of Patentability (IPRP) published Mar. 12, 2014 and Written Opinion (WO) published Mar. 6, 2014 for International Patent Application No. PCT/US2012/053943 filed Sep. 6, 2012.
Russian Decision on Granting a Patent for Invention filed on Mar. 26, 2010 for Patent Application No. RU2011141339 filed on May 10, 2013.
Office action dated Jan. 23, 2013 for Israeli application No. 215355.
Response to office action dated Jul. 2013 for Israeli application No. 215355.
Response to Mexican Office Action dated Feb. 4, 2014 for Mexican Application No. MX/a/2011/010069 with English translation.
Office Action dated Mar. 31, 2014 for Mexican Application No. MX/a/2011/010069.
First Office Action for Chinese Application No. 201080016524X with English translation from Chinese associate dated Nov. 20, 2012.
Response to First Chinese Office Action for Application No. 201080016524X dated Jun. 5, 2013.
Second Office Action for Chinese Application No. 201080016524X with English translation from Chinese associate dated Jul. 25, 2013.
Response to Second Chinese Office Action for Application No. 201080016524X dated Dec. 5, 2013.
Third Office Action for Chinese Application No. 201080016524X with English summary from Chinese associate dated Feb. 27, 2014.
Official action from European Patent Office for EP 05 803 150.1-1651 dated Nov. 16, 2011 (related application).
Response to official action from European Patent Office for EP 05 803 150.1 dated Mar. 26, 2012 (related application).
Second official action from European Patent Office for EP 05 803 150.1 dated Feb. 20, 2014 (related application).
Response filed with European Patent Office confirming applicant wishes to proceed for EP 05 803 150.1 dated Dec. 20, 2010 (related application).
Response to Mexican office action dated Jun. 9, 2014 for Mexican Patent Application No. MX/A/2011/010069.
Comunication dated Dec. 10, 2018 from European Patent Office with Supplementary European Search Report dated Nov. 30, 2018 for European Application No. EP 16789803.
Supplementary European Search Report dated May 18, 2010 for Application No. EP05803150.
International Search Report published on Nov. 2, 2006, for PCT/US2005/33769, filed Sep. 19, 2005.
International Preliminary Report on Patentability published Mar. 20, 2007, for PCT/US2005/33769, filed Sep. 19, 2005.
Written Opinion published on Mar. 20, 2007, for PCT/US2005/33769, filed Sep. 19, 2005.
International Search Report dated Apr. 10, 2008, for PCT/US2007/80262, filed Oct. 3, 2007.
Written Opinion dated Apr. 10, 2008, for PCT/US2007/80262, filed Oct. 3, 2007.
International Preliminary Report on Patentability dated Apr. 7, 2009, for PCT/US2007/80262, filed Oct. 3, 2007.
International Search Report dated Jul. 16, 2010 for PCT/US2009/066033, published Sep. 30, 2010.
Written Opinion dated Jul. 15, 2010 for PCT/US2009/066033, published Sep. 30, 2010.
International Preliminary Report on Patentability dated Sep. 27, 2011 for PCT/US2009/066033, published Sep. 30, 2010.
International Search Report dated Dec. 21, 2010 for PCT/US10/28858 filed Mar. 26, 2010.
Written Opinion dated Dec. 20, 2010 for PCT/US10/28858 filed Mar. 26, 2010.
International Preliminary Report on Patentability dated Sep. 27, 2011 for PCT/US10/28858 filed Mar. 26, 2010.
Response to the notice prior to examination for Israeli application No. 215355 filed May 12, 2014.
Notice Prior of Allowance dated Jul. 16, 2014 for Israeli application No. 215355.
Ronald Melzack and Patrick Wall, What is Gate Control Theory?, about.com Psychology, 1960.
Jul. 21, 2013 response to Jan. 23, 2013 Office Action for Israel Application No. 215355.
Response dated Mar. 12, 2014 to Office Action dated Sep. 6, 2013 for EP Application 10756926.1.
Response dated May 12, 2014 to third Office Action for Chinese Patent Application No. 201080016524.X.
Office Action for U.S. Appl. No. 13/253,572 dated Sep. 17, 2013.
Notice of Allowance dated Oct. 21, 2013 for U.S. Appl. No. 13/179,674.

(56) References Cited

OTHER PUBLICATIONS

Notice of Publication for China application No. 201280043253.6 dated Jun. 5, 2014.
International Preliminary Report on Patentability dated Nov. 7, 2017 with Written Opinion for PCT/US16/29971 filed Apr. 29, 2016.
International Preliminary Report on Patentability dated Nov. 7, 2017 with Written Opinion for PCT/US16/29938 filed Apr. 29, 2016.
Extended European Search Report dated Nov. 7, 2018 for Application No. 16789808.
Office Action dated Oct. 16, 2014 for U.S. Appl. No. 13/259,408.
Response Office Action filed Oct. 22, 2014 for Israeli Application No. 215355.
Notice of Allowance dated Oct. 2, 2014 for European Application No. 05 803 150.1-1651.
Notice of Allowance dated Oct. 6, 2014 for Mexican Application No. MX/A/2011/010069.
Response filed Oct. 26, 2015 to Office Action dated Jun. 25, 2015 for U.S. Appl. No. 13/259,408.
Office Action dated Dec. 14, 2015 for U.S. Appl. No. 14/803,535.
Final Office Action dated Jan. 20, 2016 for U.S. Appl. No. 13/259,408.
Response filed Feb. 12, 2016 to Office Action dated Dec. 14, 2015 for U.S. Appl. No. 14/803,535.
Office Action dated Apr. 8, 2016 for Korean Patent Application No. 10-2011-7025440.
Response filed Jun. 8, 2016 for Office Action dated Apr. 8, 2016 for Korean Patent Application No. 10-2011-7025440.
Notice of Allowance dated Jun. 7, 2016 for U.S. Appl. No. 14/803,535.
International Preliminary Report on Patentability dated May 31, 2016 for PCT/US2014/067587.
Apr. 13, 2018_OfficeAction_U.S. Appl. No. 15/039,898.
Communication from European Patent Office dated Jan. 24, 2018 for Application No. 16789803.0-1122.
Office Action dated Jun. 21, 2018 from Canadian Intellectual Property Office for CA Appl. No. 2864411 (national stage of PCT/US2012/053774).
Australian Patent Examination Report No. 1, dated May 5, 2014 for Patent application No. 2010229783, based on PCT/US10/028858.
Final Office Action dated Apr. 16, 2015 for U.S. Appl. No. 13/259,409.
Response filed May 21, 2015 to Final Office Action dated Apr. 16, 2015 for U.S. Appl. No. 13/259,409.
Taiwanese Office Action dated May 15, 2015 for Application No. 101132425.
Office Action dated Jun. 25, 2015 for U.S. Appl. No. 13/259,408.
Office Action dated Jun. 4, 2015 for Chinese Application No. 2012800432536.
International Search Report and Written Opinion for PCT/US16/29938 dated Aug. 25, 2016.
First Examination Report from Indian Patent Office, dated Oct. 25, 2018 for Indian Patent Application 4263/KOLNP/2011, National Stage of PCT/US2010/028858.
For U.S. Appl. No. 13/225,782: restriction requirement dated Apr. 26, 2013 and response dated Jun. 26, 2013.
For U.S. Appl. No. 13/179,674; office action dated Oct. 16, 2012; response dated Jan. 16, 2013; final office action dated Mar. 18, 2013; response dated Aug. 19, 2013.
English translation of International Preliminary Report on Patentability dated Nov. 7, 2017 with Written Opinion for PCT/US2016/029971 filed Apr. 29, 2016.
Notice Prior to Allowance dated Dec. 31, 2014 for Israeli Patent Application No. 215355.
Supplementary European Search Report dated Jan. 7, 2015 for European Application No. 12829549.
European Communication dated Jan. 23, 2015 for European Application No. 12829549.
Notice of Allowance dated Feb. 13, 2015 for U.S. Appl. No. 13/253,572.
International Search Report and Written Opinion of the International Searching Authority dated Feb. 25, 2015 for PCT/US2014/67587.
Response filed Nov. 14, 2016 in U.S. Appl. No. 14/343,085, filed Aug. 25, 2014, 13 pages.
Office Action dated Jul. 12, 2016 for U.S. Appl. 14/343,085.
Response to Final Office Action, dated Jul. 18, 2016 for U.S. Appl. 13/259,408.
Notice of Allowance for U.S. Appl. No. 13/253,572 dated Sep. 18, 2014.
Notice of Publication for HK Application No. 14108064.8 dated Sep. 26, 2014.
Office Action dated Jul. 20, 2016 for Japanese Patent Application No. JP2014-528700.
For U.S. Appl. No. 13/225,782: notice of allowance dated Sep. 5, 2013.
International Preliminary Report on Patentability published Mar. 12, 2014 for PCT/US2012/053744.
Russian Decision on Granting for Russian application No. 2011141339/02 (061869) dated Mar. 19, 2014.
Japanese Office Action dated Jan. 7, 2014 for JP 2012-502291.
Decision to Grant for JP 2012-502291 dated Apr. 17, 2014.
First Office Action dated Feb. 28, 2020 for Chinese Application No. 201680036948.X.
Response for First Examination Report dated Mar. 20, 2019, for Indian Patent Application 4263/KOLNP/2011 (18 pages).
Written Opinion dated Mar. 14, 2019 for PCT/US19/015360, filed Jan. 28, 2019.
First Examination Report dated Jul. 2, 2019, for Indian Patent Application 712/KOLNP/2014 (9 pages).
Office Action dated Nov. 14, 2019 for U.S. Appl. No. 15/571,211, 18 pages.
For Chinese Patent Application No. 201680038977X (National Stage of PCT/US2016/029971): First Office Action dated Nov. 29, 2019 Search Report dated Nov. 2019 (21 pages).
For Brazilian Patent Application No. BR112014005067-8 (National Stage of PCT/US2012/053744): Office action dated Oct. 15, 2019 (6 pages) Response filed Dec. 11, 2019 (34 pages).

\* cited by examiner

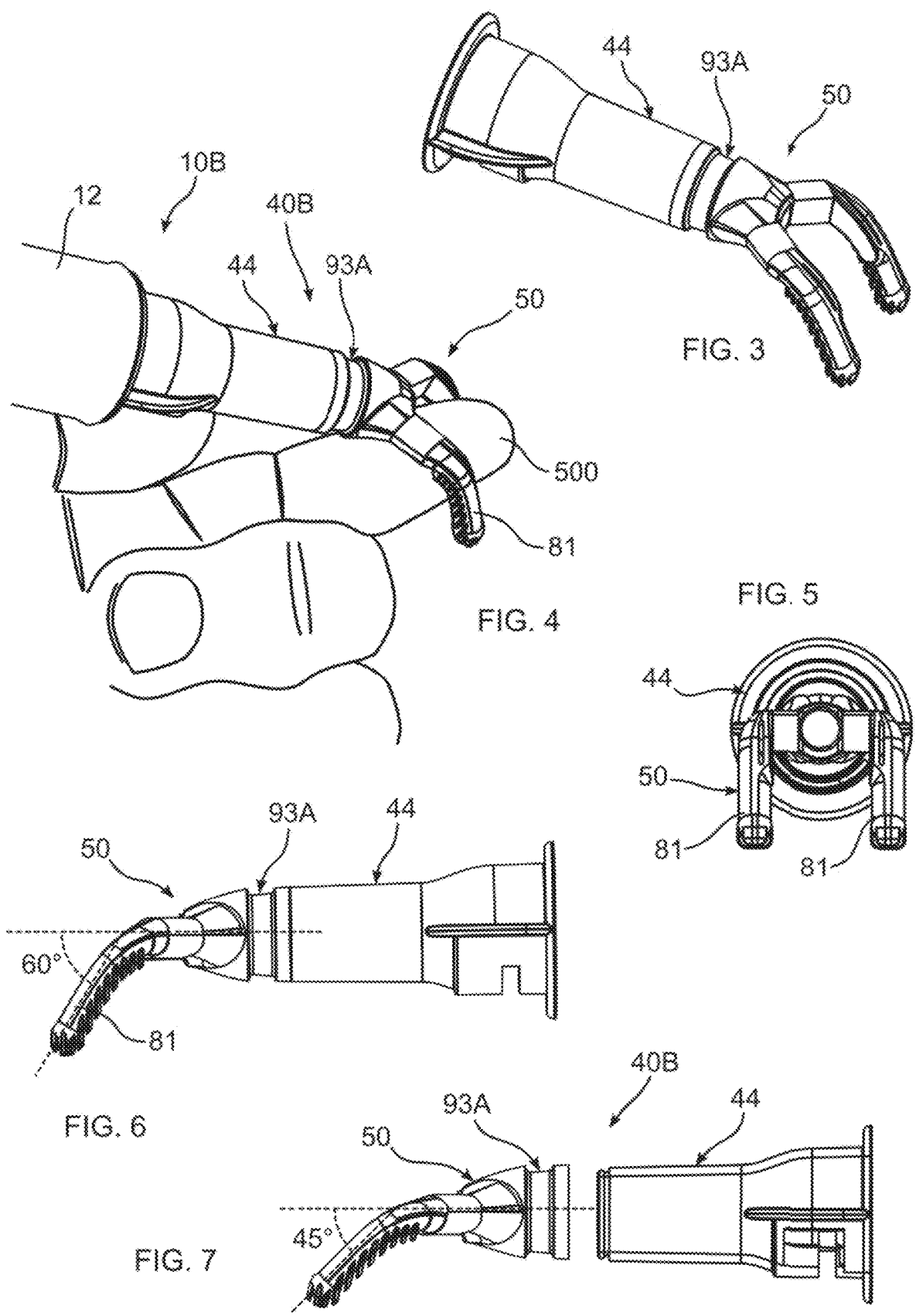

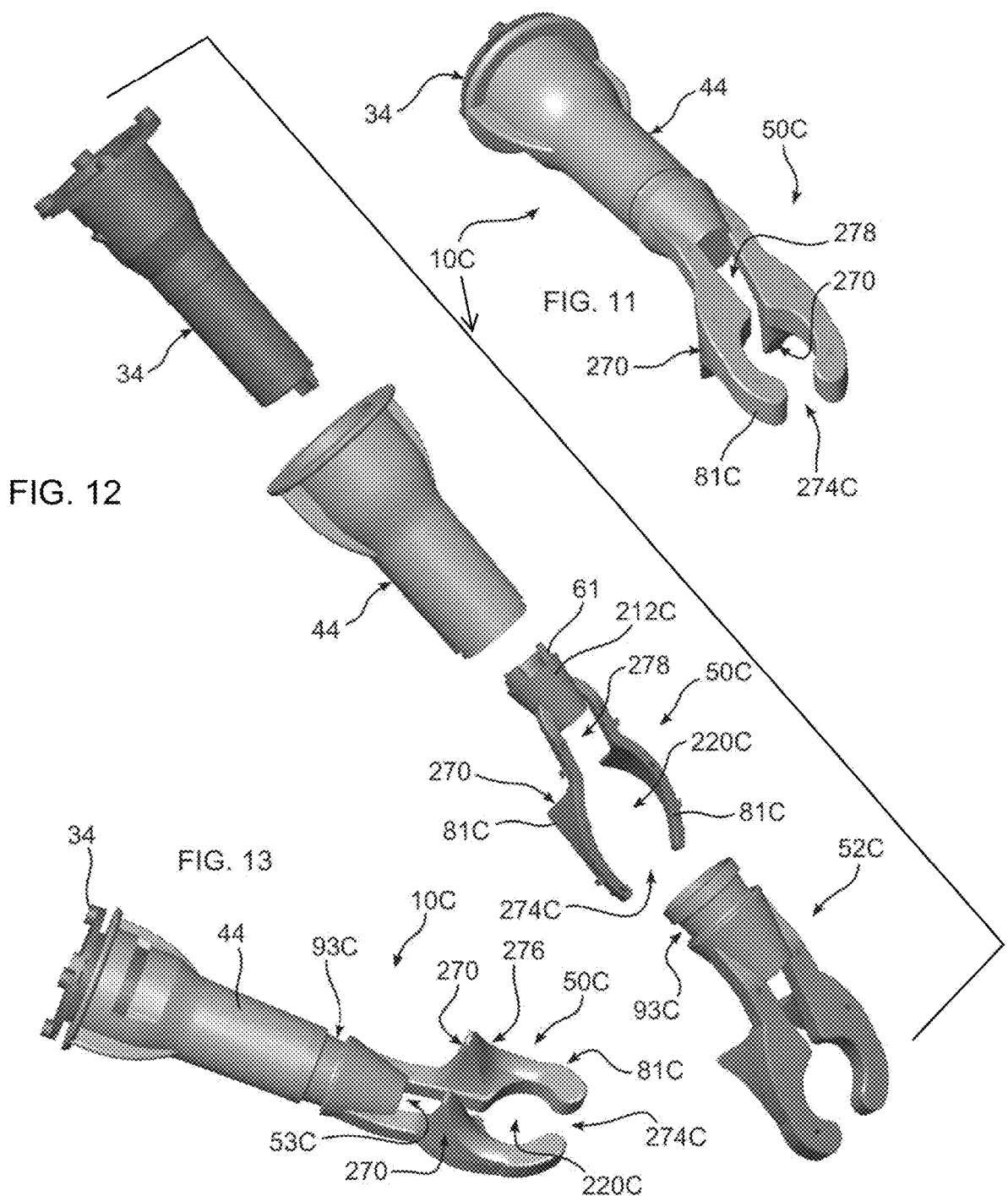

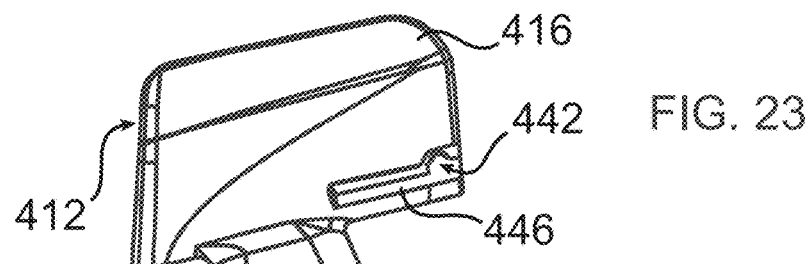
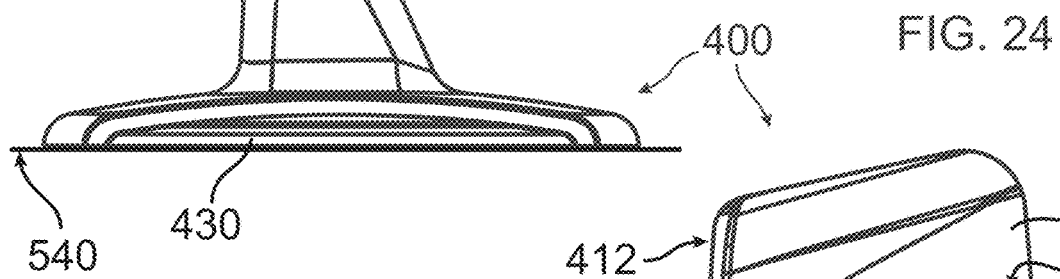
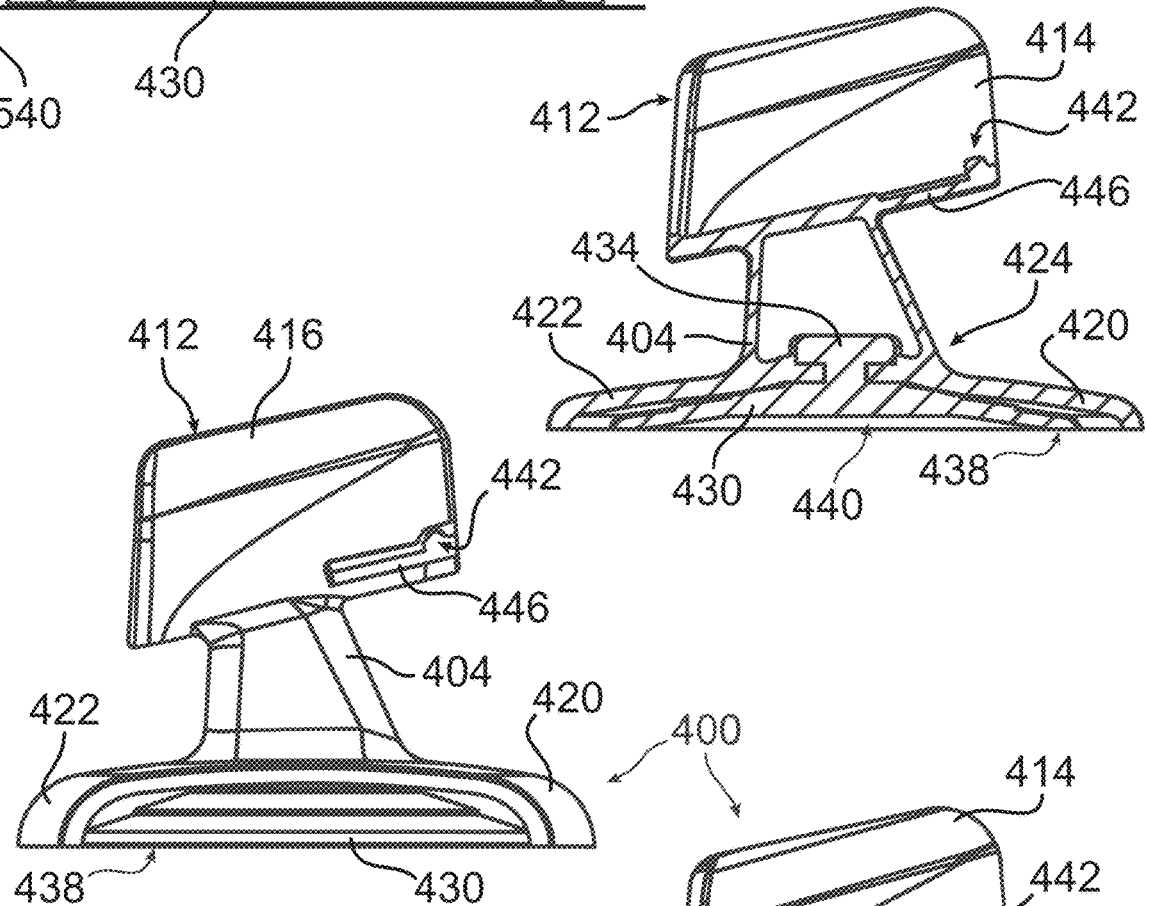
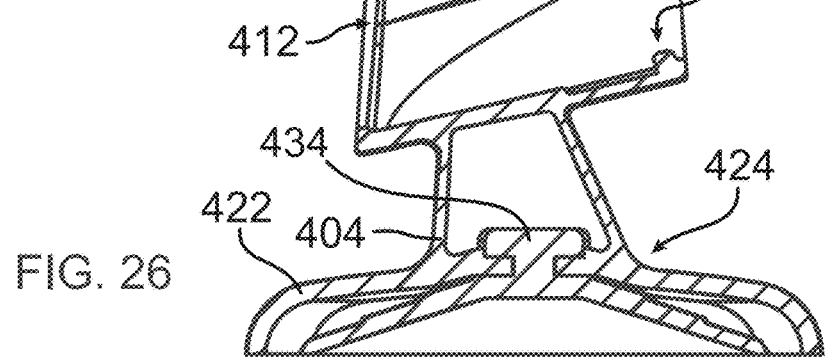

REDUCING PAIN OF SKIN PIERCING USING VIBRATION

CROSS REFERENCE TO RELATED APPLICATIONS

This application is related to:
U.S. Patent Application 60/661,497 filed Sep. 20, 2004;
U.S. Patent Application 60/707,754 filed Aug. 12, 2005;
PCT Application PCT/US05/33769 filed Sep. 19, 2005;
U.S. Patent Application 61/163,945 filed Mar. 27, 2009;
PCT Application PCT/US09/66033 filed Nov. 29, 2009;
PCT Application PCT/US10/28858 filed Mar. 26, 2010;
U.S. patent application Ser. No. 13/179,674 filed Jul. 11, 2011, now U.S. Pat. No. 8,668,664;
U.S. patent application Ser. No. 13/225,782 filed Sep. 6, 2011, now U.S. Pat. No. 8,662,952;
U.S. patent application Ser. No. 13/253,572 filed Oct. 5, 2011;
PCT Application PCT/US12/53744 filed Sep. 5, 2012;
U.S. Patent Application 61/531,264 filed Sep. 6, 2011;
PCT Application PCT/US12/53943 filed Sep. 6, 2012;
U.S. Patent Application 61/909,544 filed Nov. 27, 2013;
PCT Application PCT/US14/67587 filed Nov. 26, 2014;
U.S. Patent Application 62/155,769 filed May 1, 2015;
U.S. patent application Ser. No. 14/803,535 filed Jul. 20, 2015; and
U.S. Patent Application 62/208,860 filed Aug. 24, 2015.
the contents of all of which are hereby incorporated herein by reference in their entirety.

FIELD OF THE DISCLOSURE

The disclosure relates to a system and method for vibrating a body part to reduce pain during piercing of the skin, and more particularly to applying vibration using a handheld tool with a vibrating tip.

BACKGROUND OF THE DISCLOSURE

Procedures for reducing pain when injecting a material into the body, removing a body fluid or body tissue, or otherwise piercing the skin, include (a) placing a very cold material against the skin or flesh of the patient at the piercing site, (b) applying a topical treatment to the skin or flesh at the piercing site, which temporarily numbs the skin or flesh or (c) rapidly manually massaging the skin or tissue at the injection site while performing the injection.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings, wherein:

FIG. 3 depicts an alternative replaceable tip of the disclosure including a V-shaped distal end;

FIG. 4 depicts the tip of FIG. 3 connected to a device of the disclosure, applied to a body part of a patient;

FIG. 5 depicts a front view of the tip of FIG. 3;

FIG. 6 depicts a side view of the tip of FIG. 3;

FIG. 7 depicts a side view of the tip of FIG. 3, modified to have an alternative arm angle, and illustrating an alternative non-unitary tip having a separable distal end and base;

FIG. 11 is a top perspective view of an alternative replaceable tip of the invention, dimensioned to engage a body part and a tool end;

FIG. 12 is an exploded view of the tip of FIG. 11;

FIG. 13 is a bottom perspective view of the tip of FIG. 11;

FIG. 23 is a side view of the holder of FIG. 20, where the holder has been pressed against a surface to activate a suction cup of the holder, and to spring-load a resilient frame of the disclosure;

FIG. 24 is a cross-sectional view of the holder of FIG. 23, taken along line A-A of FIG. 20;

FIG. 25 is a side view of the holder of FIG. 20, with the suction cup engaged with a surface, and with the frame exerting a pulling force against the suction cup, while engaged with the surface; and FIG. 26 is a cross-sectional view of the holder of FIG. 25.

DETAILED DESCRIPTION OF THE DISCLOSURE

Figure 1:
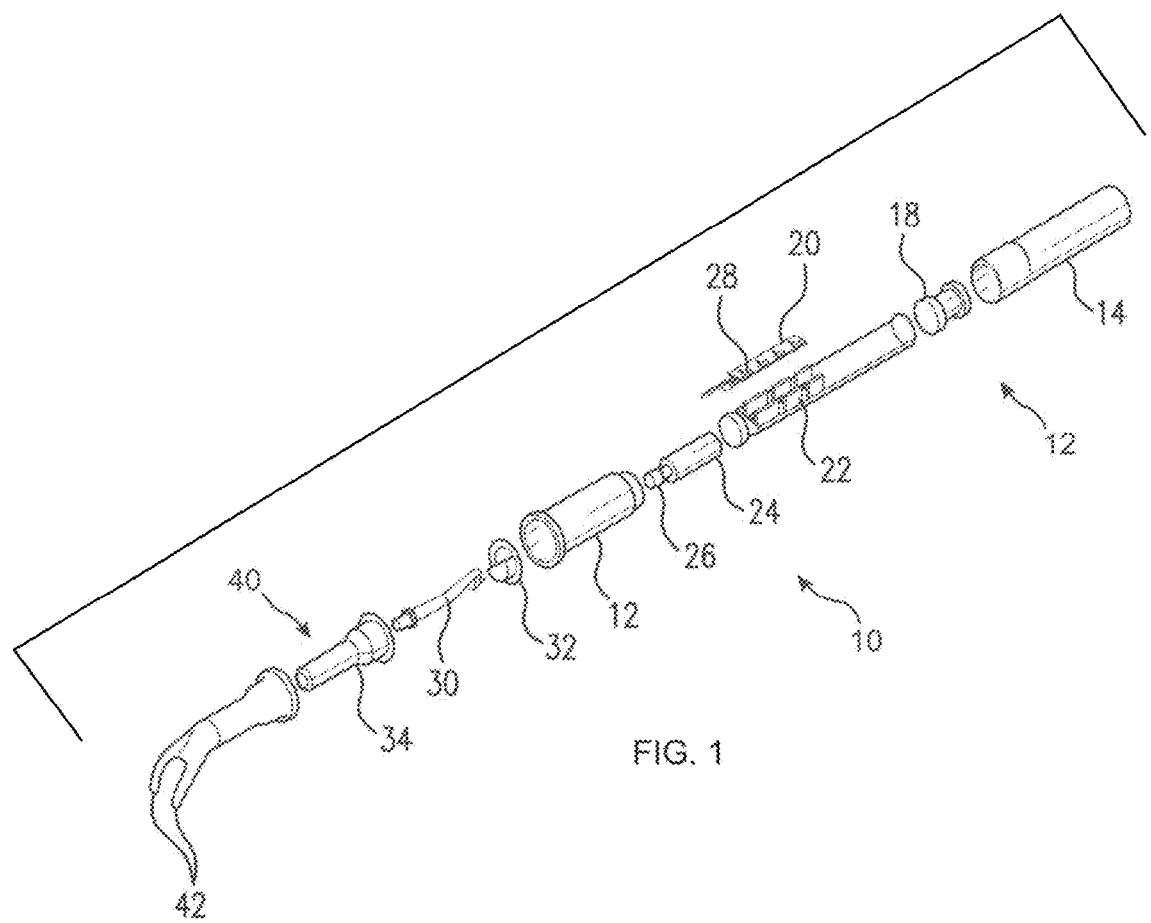
FIG. 1 is an exploded drawing showing an embodiment of the apparatus of the present disclosure.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one, or more than one. The term plurality, as used herein, is defined as two, or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The disclosure reduces pain to a patient being injected, for example with an anesthetic, serum, vitamins, vaccine, or other medically efficacious liquid. The disclosure can be easily and inexpensively utilized during a medical, veterinary or dental procedure to almost completely or substantially eliminate the pain attendant an injection as it punctures the skin or flesh of the patient. The disclosure overcomes the cumbersome, time consuming aspects of the prior art, including providing a more efficacious effect, more often reducing pain to an acceptable level. The disclosure also reduces pain when a body fluid is withdrawn from a patient, for example using a lancet or hypodermic needle and syringe.

The disclosure reduces pain to a patient being injected, for example with an anesthetic, serum, vitamins, vaccine, or other medically efficacious liquid. The disclosure can be easily and inexpensively utilized during a medical, veterinary or dental procedure to almost completely or substantially eliminate the pain attendant an injection as it punctures the skin or flesh of the patient. The disclosure also reduces pain due to any disturbance of the skin our underlying tissues, for example the pain which accompanies puncture of the skin associated with removal of fluids from the body. Examples include while removing blood for a glucose test or other blood analysis; during a puncture associated with treatment of the skin, such as acne or blisters; and for other fluid withdrawals, for example during phlebotomy, paracentesis, aspiration, or synovial fluid withdrawal.

The disclosure provides a disposable tip and a hand-held apparatus, which in an embodiment has the form of an instrument, for vibrating a skin or tissue area. Aspects of the disclosure are described in the incorporated applications. In various embodiments, a vibrating end contacts at least two skin or tissue areas, or a circular skin or tissue area, immediately at an injection site or site of a painful contact, and do so while the painful act takes place. Pain can be caused by injection, for example of a liquid anesthesia, serum, vitamins, vaccine, or other medical or dental efficacious material, into the skin or tissue at the injection site. Typically, a region of interest for a dentist can be the entire oral mucosa area and underlying bone, whereas the region of interest for a medical doctor can be the whole body and underlying bone. The disclosure is applicable to both practitioners, for any area of the body. For a dentist, a typical injection procedure may involve an injection of Lidocaine into a patient's gum or other tissue during a dental procedure.

The method of the disclosure consists in vibrating tissue of a human or animal in proximity to a preselected injection site on the human or animal body while simultaneously injecting by a needle or like instrument a liquid at the preselected injection site. The vibration can be effective if transmitted to a circular or other shaped area of body tissue, which can include bone underlying skin at an injection site, and particularly on opposite sides of injection site.

In various embodiments of the disclosure, reuse of an endpiece such as a vibrating tip of the instrument is prevented, to avoid cross-contamination between patients. In one embodiment, the tip is broken when removed. In another embodiment, electromagnetic communication is established between an electronic tag on a tip and an electronic circuit within the body of the instrument. In this manner, a use count and validation of the tip can be monitored, and activation of the instrument can be disabled if the tip should be replaced after a period of time, or a predetermined number of uses, which are indicative of potential reuse between patients.

The embodiment disclosed herein is a tool for relieving pain associated with an injection, or any other piercing of the skin. For example, in addition to injections, the disclosure applies to other pain inducing procedures applied to any body tissue, such procedures including cauterizing, application of laser light, application of chemicals, or insertion of sutures, clips, or staples, or to pierce the skin to withdraw a sample of a body fluid. Further, it should be understood that the disclosure can be used to control the use of any tool tip, whether used in dentistry, general medicine, or within an industrial application, for example a grinding or boring machine tool tip, or other end effector.

Figure 2:
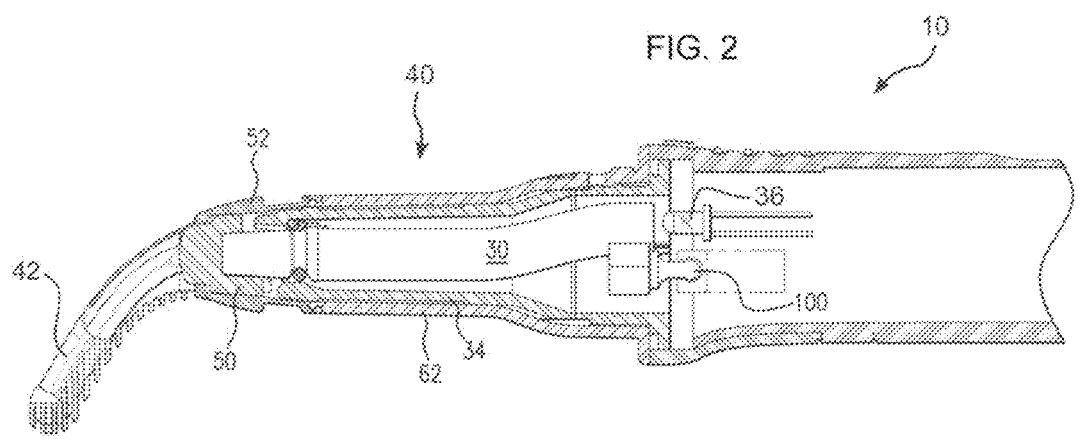
FIG. 2 is an assembly view in section of a disposable tip mounted on the handle sleeve of an instrument of the disclosure.

Referring to FIGS. 1 and 2, an embodiment of a vibrating tool is shown generally designated as instrument 10 for performing the functions of the present disclosure, as will be explained hereinafter. In particular, instrument 10 is a hand-held apparatus comprising a main frame, body or handle 12 in the shape of a tube having a battery cover 14 as an end closure that is threaded to screw onto the open end of handle 12 in a complementary fit. Handle 12 is composed of hard plastic or other sufficiently rigid material, and partially receives a chassis 22, the uncovered portion being covered by the battery cover 14. One or more rechargeable batteries are located in battery compartment 16 of chassis 22. An induction coil 18 is mounted on the end of chassis 22 and positioned in the battery cover 14 to couple to a charge device in a conventional manner. An external power source can be connected to instrument 10 by a wire, to charge an internal battery, to power the device in the absence of a battery, or to power the device while a battery is charging.

A motor 24 driving a cam 26 is housed in the handle 12. Cam 26 includes a bore in the form of a ball socket whose axis is offset from the motor drive axis. The vibration induced by the cam 26 and follower 100 is transmitted via a polycarbonate light rod 30 to polycarbonate tip frame 50 and will produce vibrations at the free ends of the two bifurcated legs 42 of tip frame 50. It should be understood that polycarbonate can be replaced with any other material of sufficient rigidity and light transmitting ability. It should be further understood that alternative means of producing vibration can be provided, including for example reciprocating mechanisms, electromechanical actuators, and acoustic or other vibrating transducers, or other types, as known or hereinafter developed.

During vibration, the light rod 30 pivots about a resilient mounting, enabled in an embodiment by a resilient O-ring, at the end of nozzle 34 which can hold the light rod 30 relative to nozzle 34 so that it can vibrate freely. A PCB board 20 containing electrical and electronic circuitry 28 is mounted on the chassis 22. The battery is connected via the circuitry 28 to control the motor 24 in the manner described in one or more of the prior applications incorporated herein by reference. When the motor 24 is driven, vibration produced by the cam 26 is coupled to polycarbonate light rod 30 via a coupling fitting and cam follower.

The forward end of the handle 12 has an adapter 32 fixed to the chassis and the handle. A nozzle 34 is fixed to the adapter 32. The light rod 30 is received in the nozzle 34 and is resiliently coupled to it at its forward end. The nozzle 34 receives an endpiece, in this embodiment a disposable tip 40 comprised of three components, namely, a forward vibratable tip 50 detachably and rigidly mounted on the end of light rod 30 to transmit vibrations, with tip 50 having, among various configurations, a bifurcation at its forward end; a tip sleeve 62 for detachably and rigidly mounted on nozzle 34; and an overmold 52 that holds tip 50 and sleeve 62 together and enables tip 50 to vibrate freely relative to sleeve 62. An LED 36 is mounted to the PCB 20 as shown in FIG. 2, disposed to transmit light into light rod 30 during vibration of light rod 30.

The incorporated references detail various embodiments of instrument 10, including an electromechanical interlock to prevent excessive reuse of tip 40; the function of overmold 52 for transmitting vibration and connecting legs 42; a mechanical connection which cuts overmold 52 during removal of tip 42 to prevent reuse; a ball end 100 and cam 26 connection for generating vibration; pulsation of vibration with varying on/off times; various tip end 42 shapes and configuration; an instrument 10 charging stand and inductive charger; a toy adapter; a noise generator; applying pressure after piercing tissue; various angular dispositions of the tip ends 42; a light shone between tip ends 42; a music player incorporated into instrument 10; an RFID or near field tag associated with tip 40 in communication with an antenna and processor connected to the handle 12.

It should be apparent to one skilled in the art, from the above description and the incorporated references, that the present disclosure can be utilized in a variety of procedures requiring a skin or flesh puncture, abrasion, or other potentially painful treatment. Such other procedures include therapeutic inoculations, including shots to give patients medication, or to draw blood or fluids, and other procedures. Such procedures can be performed on any portion of the body such as the arm, legs, buttocks, torso, etc.

With reference to FIGS. 3-7, an embodiment of tip 40B which does not include overmold 52 is illustrated, although other embodiments described herein can be used in the illustrated application. More particularly, frame tip or distal tip 50 includes two longitudinally extending arms 81 which form a V-shape. This shape enables any narrow body part, including for example a tendon, toe, thumb, muscle, ear, nose, cheek, tongue or other mouth part, brow, or finger 500, to be inserted between the arms 81 of the V until contacted on opposite sides of the body part. In this manner, and as may be seen in FIG. 4, a single size of distal tip 50 can accommodate a range of sizes and parts. Additionally, distal tip 50 can be provided in a variety of sizes and shapes.

Further, as shown in FIGS. 6 and 7, arms 81 can be disposed at various angles with respect to handle 12. This angle can be selected to enable handle 12 to be positioned at a comfortable distance from the body when arms 81 are applied to the body. The angle can further be selected to foster a comfortable posture of the practitioner or patient when holding handle 12 when positioning a particular body part within arms 81. In the example of FIG. 6, an angle of 60 degrees is illustrated, and the example of FIG. 7, an angle of 45 degrees is illustrated. It should be understood that this angle can be any angle, selected to facilitate positioning arms 81 in contact with a desired body part, in consideration of the relative position of the person holding handle 12, and in consideration of the manner in which arms 81 and other part of tip 40 should contact the body part to be desensitized to pain. FIG. 7 further illustrates that tip 40B can be produced in separable components, although it should be understood that tip 40B can also be produced as a unitary part including base 44 and tip 50.

Once distal tip 50 contacts the body part which is expected to experience pain or discomfort, vibration can be initiated and continued as described herein. As described herein, this vibration can be at any of a range of frequencies, or along a range of frequencies, and a particular frequency or range of frequencies can be programmed or provided which best demonstrates efficacy to reducing pain associated with piercing or treating a particular body part, and/or a body part with particular characteristics, for example relating to skin thickness or sensitivity. As further described herein, the vibration can be pulsed or discontinuous.

Without being bound to any particular theory, as nerves proximate skin contacted by vibrating arms 81 are stimulated, nerve conduction associated with pain or discomfort is diminished. At this point, skin between or adjacent arms 81 can be pierced, abraded, treated with a chemical or medicament, or otherwise disturbed in a manner which tends to produce pain or discomfort. Vibration can be discontinued after an amount of time has passed whereby an initially high level of pain or discomfort would normally be expected to be sufficiently abated.

Figure 8:
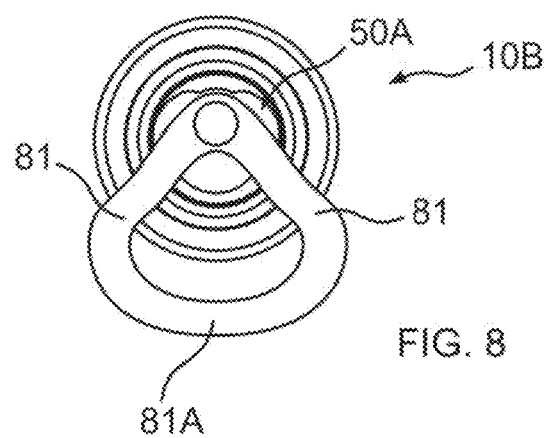
FIG. 8 depicts an alternative distal end forming a closed loop.
Figure 9:
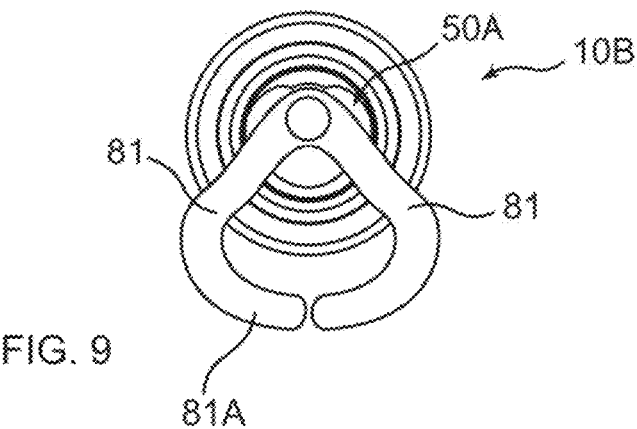
FIG. 9 depicts an alternative distal end having arms which form a divided loop.

With reference to FIG. 8, it may be seen that distal tip 50A is provided with a lateral arm 81A which forms a closed loop between arms 81. In this manner, an inserted body part, such as finger 500 in FIG. 10, can be contacted at multiple points surrounding a site of pain or discomfort. Further, a loop can be used to retain the body part in contact with the vibration, which can be helpful for fearful or otherwise movement prone patients. Lateral arm 81A can also be provided with a gap 274, as shown in FIG. 9, which can enable arms 81A to bend to accommodate larger body parts, or to more resiliently contact the body part on opposing sides.

Figure 10:
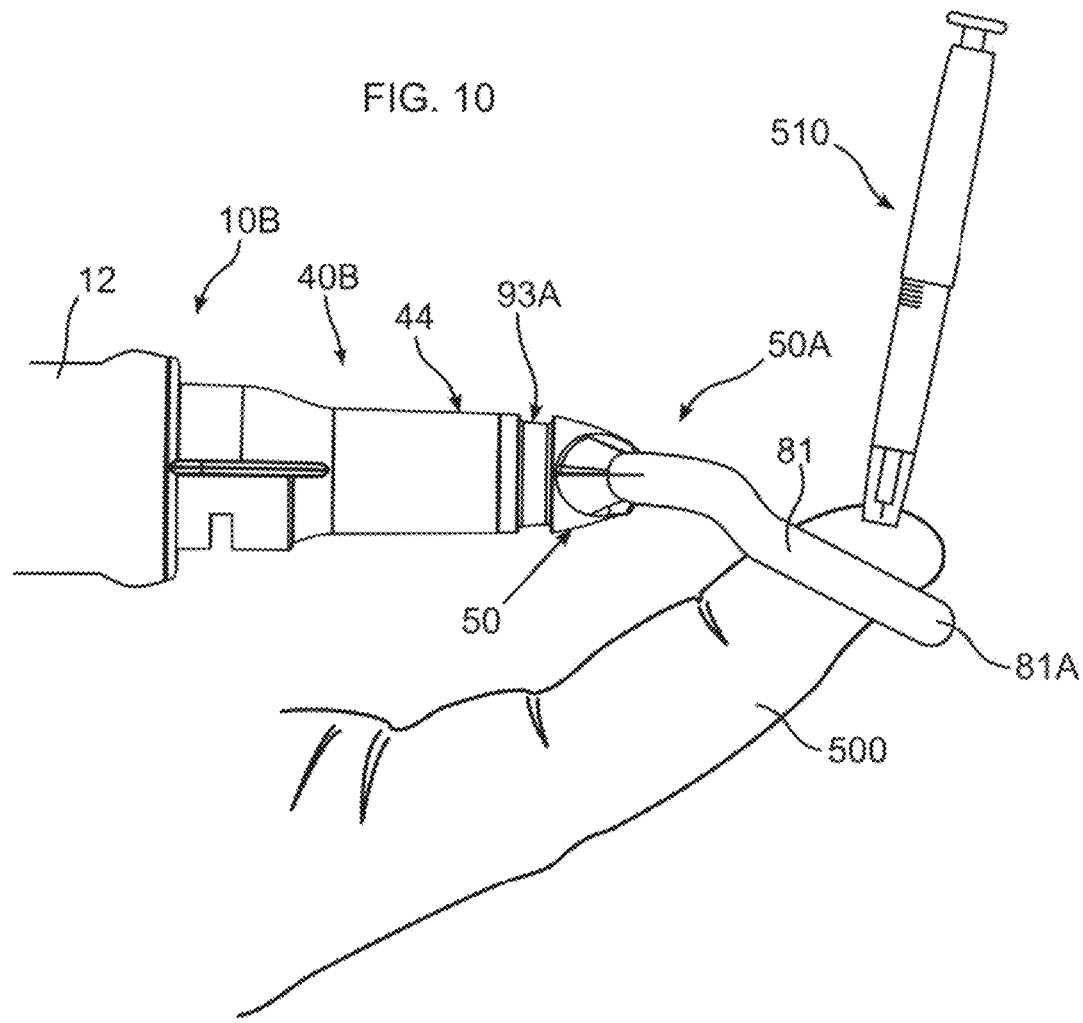
FIG. 10 illustrates the distal end of FIG. 8 used to apply vibration to a body part prior to and during a lancing procedure.
Figure 14:
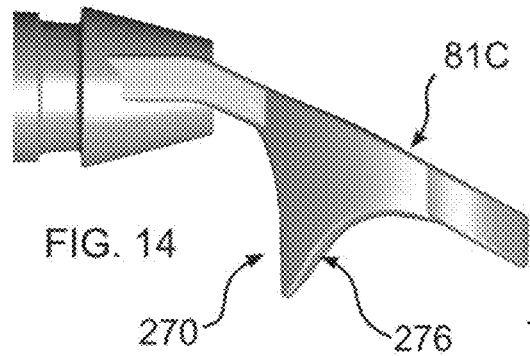
FIG. 14 is a side view of the tip of FIG. 11.
Figure 15:
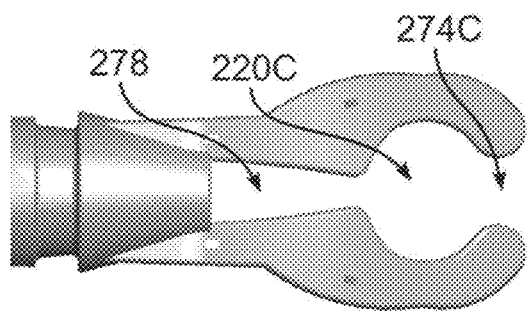
FIG. 15 is a top view of the tip of FIG. 11.
Figure 16:
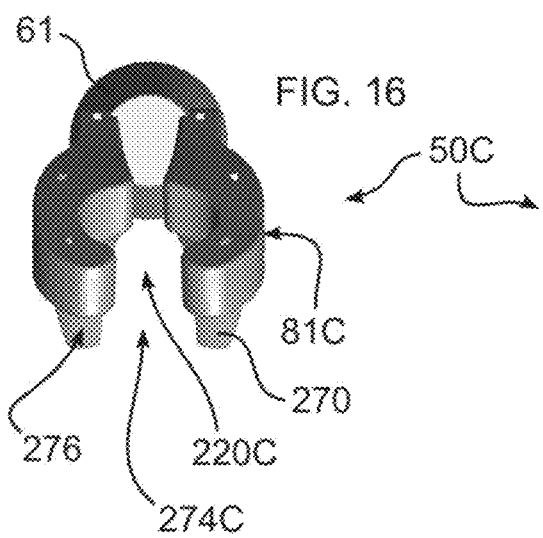
FIG. 16 is a front perspective view of the tip of FIG. 11.
Figure 17:
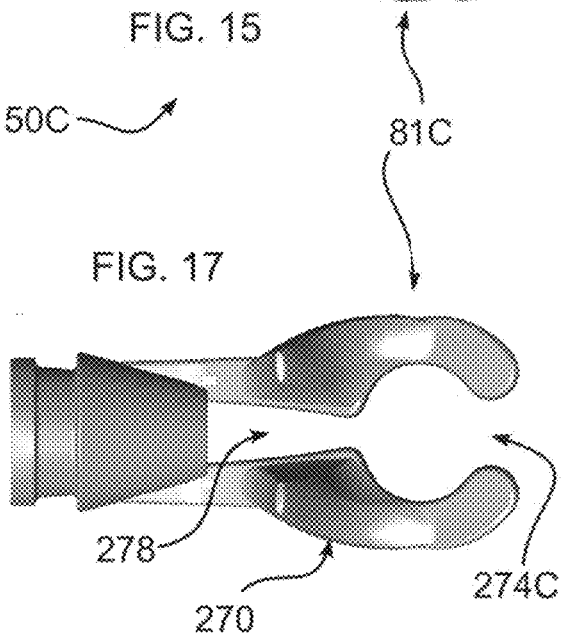
FIG. 17 is a bottom view of the tip of FIG. 11.
Figure 18:
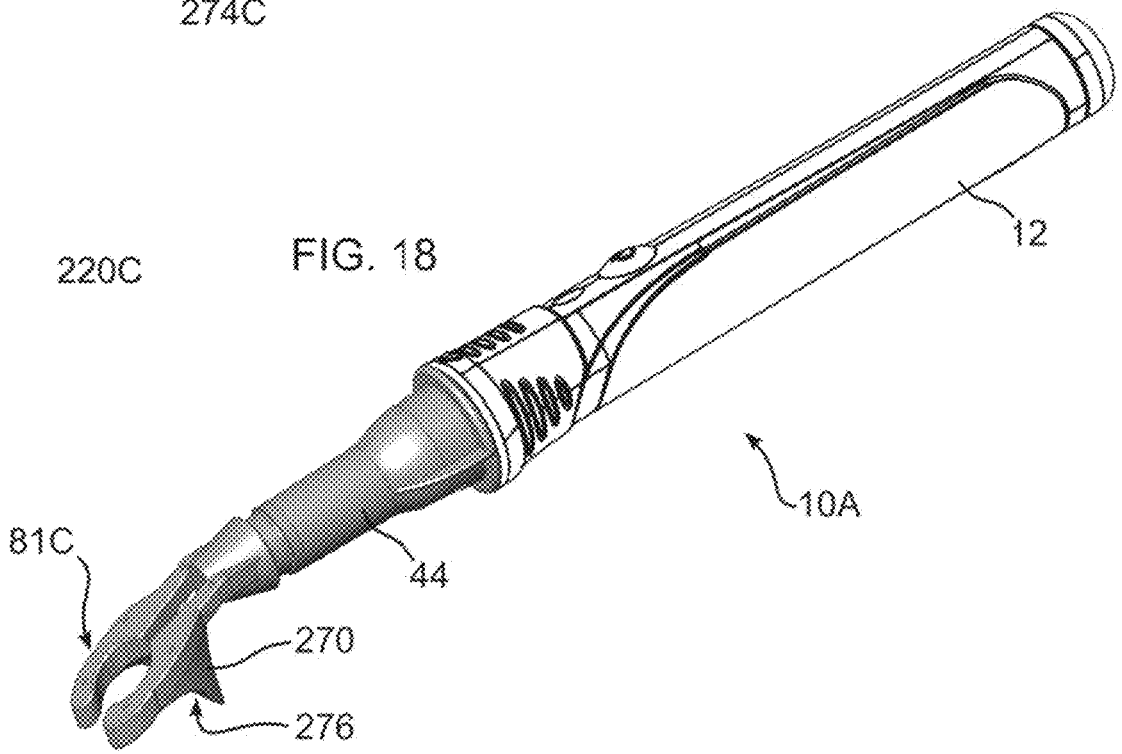
FIG. 18 is a perspective view of the tip of FIG. 11 connected to a remainder of an instrument of the disclosure.

In FIG. 10, instrument 10B is shown applied to a finger 500, which is about to be pierced by lance 510, in order to obtaining a blood sample for a therapeutic application, such as glucose monitoring. It may be seen that finger 500 is inserted within distal tip 50A, although any other tip of the disclosure which can accommodate a finger can be used. In this example, finger 500 is pressed into the narrow portion of the V shape to increase contact with distal tip 50A, to better convey vibration to the skin of finger 500. Vibration is applied to the finger at intervals and frequencies described elsewhere herein and in the incorporated references, and the finger is lanced with reduced discomfort and pain, after which vibration can be terminated, and the finger 500 can be removed from distal tip 50A.

Referring now to FIGS. 11-18, an instrument 10C include a distal tip 50C configured to cooperate with a skin piercing device. Instrument 10C further includes a nozzle 34 and tip sleeve or base 44, which function in a manner as shown and described for any of the embodiments herein, including for example as described for instruments 10 and 10A. A distal tip 50C includes a cup 212C including positive ribs 61 or any other form of coupling with nozzle 34 as described herein or as may otherwise be carried out to transmit vibration to distal tip 50C. In an embodiment, the distal tip 50C can be provided with tag 370 and antenna 302 and associated components as described with respect to instrument 10A.

Distal tip 50C is provided with a body contacting profile 270, which are shaped to receive a body part which is to be pierced or is otherwise to be subjected to a potentially painful procedure. In the embodiment illustrated, portions 270 are configured to be contacted by an end of a finger 500 of a hand, or a toe of a foot of a patient. It should be understood that the disclosure is not limited to reducing pain in fingers, however, and that contacting profile 270 can be sized and shaped to be engaged by any body part. Contacting profile 270 is shaped to guide the body part into vibration transmitting contact with tip 50C, and to reduce the likelihood of movement of the body part during the procedure by contacting the body part along differing areas thereof. Arms 81C extend past contacting profile 270 and cooperate therewith to support and guide the body part.

In the embodiment shown, contacting profile 270 is provided in two parts, each associated with one of arms 81C, and each extends substantially transverse with respect to a plane defined by arms 81C, although profile 270 can project therefrom at any angle which bests accommodates the desired body part. A shaped surface 276 forms a curve which corresponds to the shape of the end of human finger, whereupon arms 81C support a fingertip pad portion of the finger. Shaped surface 276 further has angled surfaces which are mutually facing and which function to center the finger within tip 50C, whereupon a center of the fingertip pad is positioned to be exposed by space 220C, through which the procedure may be conducted.

The various surfaces of tip 50C can be formed directly upon a unitary molded part, or can be formed upon a surface of an overmold 52C. In the latter configuration, tip 50C forms an inner supporting frame which supports overmold 52C, and limits deformation and bending thereof. Overmold 52C can be made of plastic, neoprene, silicone rubber, latex, or any other material which confers beneficial properties upon tip 50C, which can include any or all of biocompatibility, ease of cleaning, comfort to the patient, a secure non-slip engagement with the body part, an attractive color, a more easily moldable complex curved shape, a seal with nozzle 34, and a vibration transmitting coupling with nozzle 34. Overmold 52C can include an opening proximate lens 53C or other opening in cup 61 through which light may be transmitted. It should be understood, however, that tip 50C can be molded as a unitary part from similar materials providing the same beneficial properties.

In the embodiment shown, arms 81C are separated from each other by a gap 274C, which promotes the conduction of vibration along the entirety of arms 81C, including contacting profile 270. Further, arms 81C are resilient, and can be bent relatively apart to admit passage of, and thereby better grip, a portion of a body part, directing the vibration into the body part. Arms 81C can be disposed at an angle relative to handle 12 as described elsewhere herein with respect to other tip arms.

Figure 19:
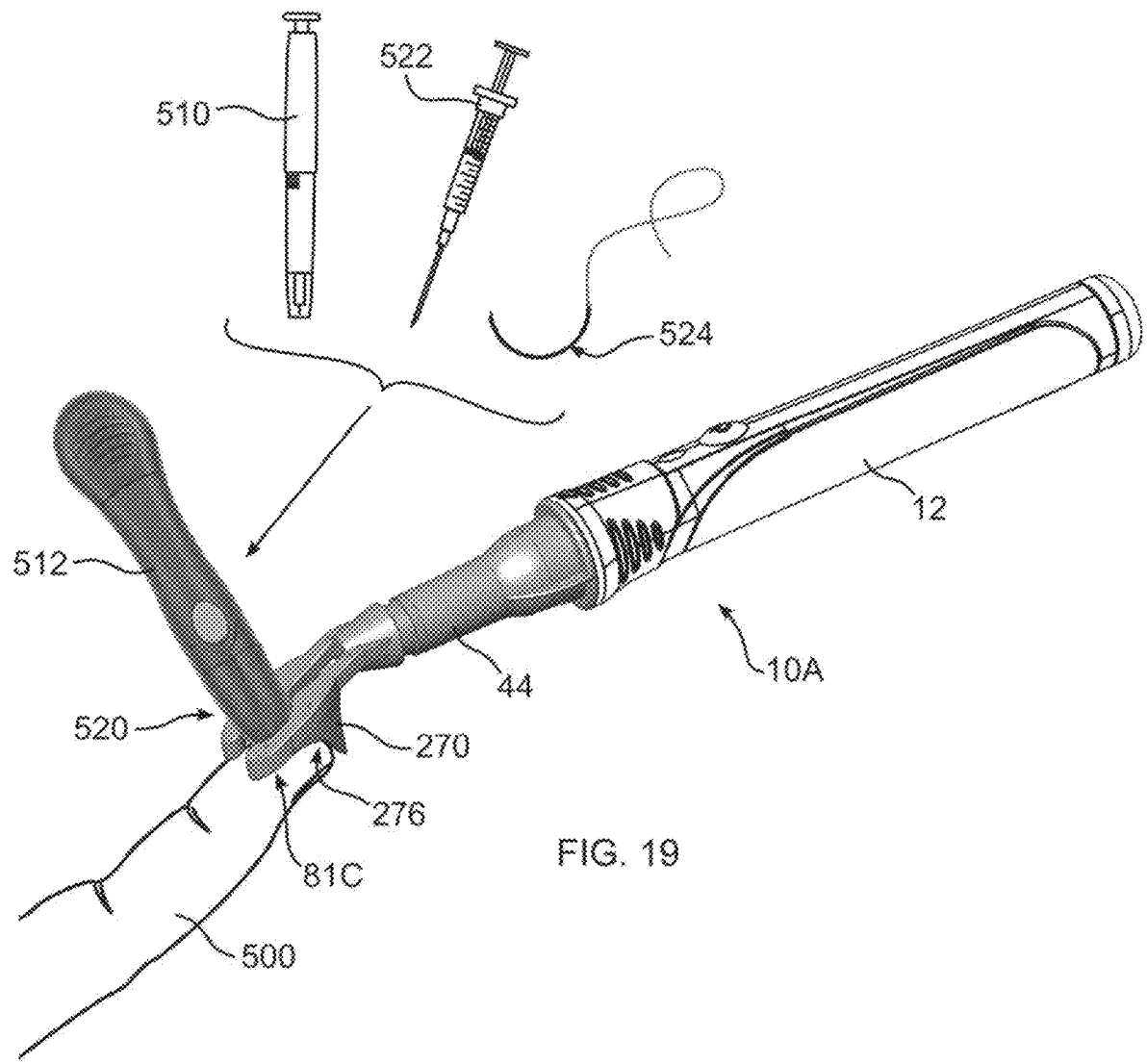
FIG. 19 is a perspective view of the instrument of FIG. 18 being used to position a prior art lance device in relation to a finger of a patient for a therapeutic procedure in which the instrument reduces pain of the procedure.

In an embodiment of the disclosure, arms 81C and space 220C are sized and dimensioned to engage a tool which will be used to carry out a therapeutic procedure for a patent, including for example obtaining a blood sample, as shown in FIG. 19. More particularly, in the example of FIG. 19, arms 81C are shaped to surround almost entirely, and positively position, a lancing device 512 which has a tapered round end 520 shape. Arms 81C thereby ensure that an area of skin which is to be pierced is optimally located with respect to arms 81C to ensure that vibration extends around the area of skin to be pierced, thereby ideally impacting nerve sensations associated with the area to be pierced. Absent this mating fit, it would be possible to pierce the skin more towards one arm 81C or another. While this may be effective for many purposes, it may in some instance be advantageous to ensure that the piercing will be equidistant from both arms, and in a center of space 220C, which is accomplished by the mating fit of arms 81C and a mating end 520 of a particular style of lancing device. It should be understood that tip 50C can be configured to only engage a body part using a contacting profile 270, or only engage a tool end using shaped arms 81C, or can be configured to do both, as illustrated.

In the manner discussed above, arms 81C can resiliently bend to admit passage of the mating tool end 520, and thereafter resiliently apply a force towards an original position of arms 81C to thereby grip the tool end 520 to help maintain its position with respect to the body part during use of the tool 512. Tip 50C can also be formed with arms 81C connected as shown in the embodiment of FIG. 8, and may still resiliently grip and mate with an inserted tool end. Alternatively, arms 81C can be rigid, and either unconnected or connected, yet can form a mating relationship with one or more tool ends.

To enable greater flexibility to accommodate a wider set of tool sizes which can be inserted between arms 81C, and/or to facilitate resilient bending of arms 81C, a leading gap 278 can be provided between a base of arms 81C and space 220C. Leading gap 278 further provides a pathway for illumination to pass from lightpipe 30 to the working area proximate space 220C.

It should be understood that the cooperative relationship between arms 81C of tip 50C and a tool end is not limited to a lancing device, and can be created between tip 50C and any therapeutic tool currently known and hereinafter developed which can advantageously be positively located relative to a piercing or potentially painful site, and the application of vibration from an instrument 10 or 10A of the disclosure.

As shown in FIG. 19, a mating relationship is not required in order to convey a therapeutic, pain reducing benefit of an instrument 10, 10A of the disclosure. As shown, an alternative lance 510 end shape can be used, as well as a hypodermic syringe 522, or sutures 524, for example. Other tool ends would be apparent to a medical practitioner, and can include for example a clamp, tweezers, scissors, scalpel, or punch biopsy. Therapeutic procedures can include injecting a liquid, for example when providing a drug or vaccine, or removing fluid, for example withdrawing blood or an infection, or for applying light, for example laser light, in the treatment of skin disease. Further, tip 50C or any tip of the disclosure can also be used within a cosmetic or non-therapeutic procedure, including for example use with a tattoo needle for creating a tattoo, or a laser for removal of a tattoo, or a laser for treating the skin for wrinkles or discoloration.

With reference to FIGS. 20-26, a mounting base 400 for an instrument 10D of the disclosure includes a device stand 410, a base extension 404, instrument holder 412, support legs 420, 422, and a suction cup 430. Device holder can be sized and shaped to releasably and securely retain any instrument of the disclosure as described herein, or in the incorporated references.

Figure 20:
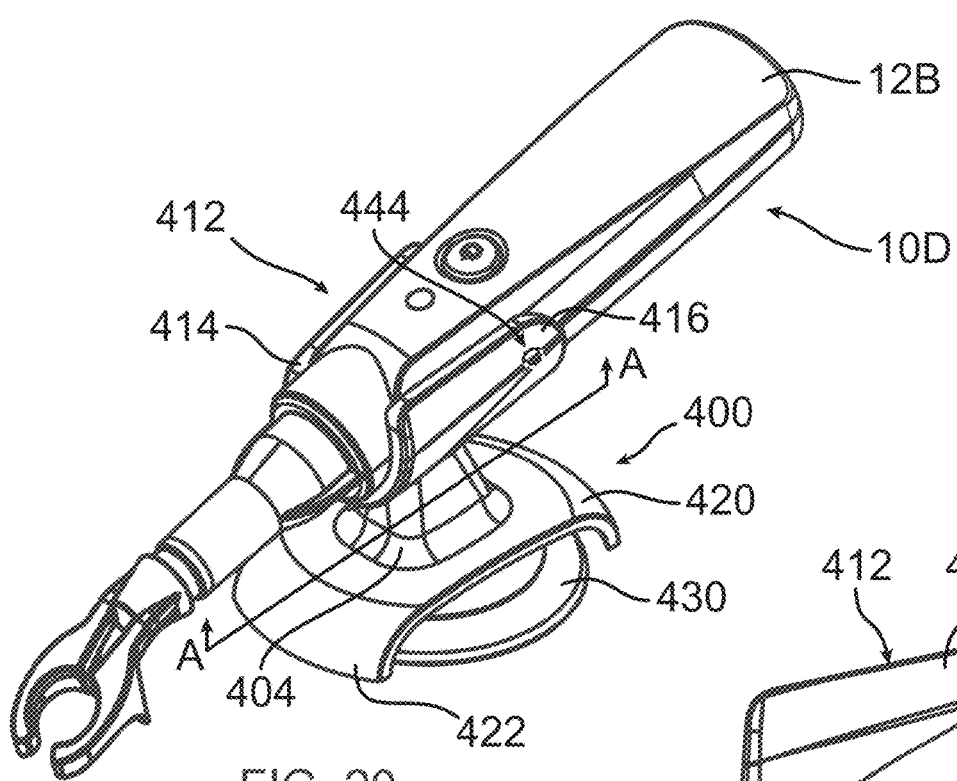
FIG. 20 is a perspective view of a holder of the disclosure holding an instrument of the disclosure.

In FIG. 20, instrument 10D further includes an ergonomically shaped handle 12B, which has a flattened profile which facilitates gripping with the hand for rotating instrument 10D to a desired optimum angle for contact of tip frame 50 with the treatment site.

Instrument holder 412 is shaped to slidingly and releaseably retain handle 12 (generally designating 12/12A/12B), and forms a tapered profile which mates with a tapered profile of handle 12, to enables insertion of instrument 10 (generally designating 10/10A/10B/10C/10D) to a desired predetermined extent, whereby a sufficient portion of handle 12 extends from holder 412 in order to enable handle 12 to be easily grasped and pulled to remove instrument 10. As an alternative to a tapered fit, handle 12 can be shaped to contact a surface of instrument 10 to prevent insertion beyond a desired predetermined extent.

In addition, or as an alternative to the foregoing, holder 412 and handle 12 can be provided with mating detent portions, such as a protrusion 442 on one part, and a recess 444 on another, which engage when instrument 10 has been inserted sufficiently. In the embodiment shown, protrusion 442 is disposed on a resilient arm 446, integrally molded with holder 412. Recess 444 is disposed within handle 12, although it should be understood that a recess can be provided within holder 412, and a protrusion can be provided upon handle 12. Further, a recess can be provided upon resilient arm 446, and a fixed protrusion can be provided upon handle 12. When instrument 10 is inserted, arm 446 bends to enable protrusion 442 to be displaced by handle 12. When protrusion 442 is aligned with recess 444, arm 446 pushes protrusion 442 into recess 444. An alignment of protrusion 442 and recess 444 can be achieved by mating surfaces in an interior surface of holder 412, and corresponding mating exterior surfaces of instrument 10, which contact each other to mutually guide and orient instrument 10 as it is inserted into holder 412.

Holder 412 includes two opposed arms 414, 416 which can be formed with a resilient material, whereby arms 414/416 can bend to enable engagement and disengagement of the detent. Alternatively, resilient arms 414/416 can be formed to define, when relaxed, an interior diameter which is smaller than a diameter of instrument 10 or handle 12, whereby a wedging force is achieved when instrument 10 has been inserted, which causes instrument 10 to be securely retained between arms 414/416 when sufficiently inserted.

Holder 412 can further be disposed at an angle with respect to a plane defined by a bottom of legs 420, 422, which are intended to rest upon a surface upon which base 400 is to be mounted. In this manner, gravity can be employed to retain instrument 10 within holder 412. In the embodiment shown, an angle of 15 degrees is formed, although any angle can be used, for example anywhere from 10 to 30 degrees, although any angle between zero and vertical, inclusive, can be used in accordance with the disclosure. In an embodiment, the angle can be selected by rotating holder 412 about a pivot (not shown) which connects holder 412 to base extension 404.

Base extension 404 increases a height of holder 412 above a surface to which device stand 400 is mounted. In this manner, tip frame 50 does not contact the surface when instrument 10 is in holder 412, and handle 12 is spaced from the surface to be easily grasped by a hand.

Legs 420, 422 extend from opposite sides of a lower portion 424 of base extension 404. While two legs are shown, any number of legs can be provided, such as 3, 4, or a large number. However, the legs are advantageously resilient, and can bend a substantial extent, as will be described in detail with respect to FIGS. 23-26. The formation of independent legs facilitates bending, however it should be understood that, in place of independent legs 420, 422, a cup-like structure could be provided, so long as the required resiliency and stability, as described below, are provided.

Figure 21:
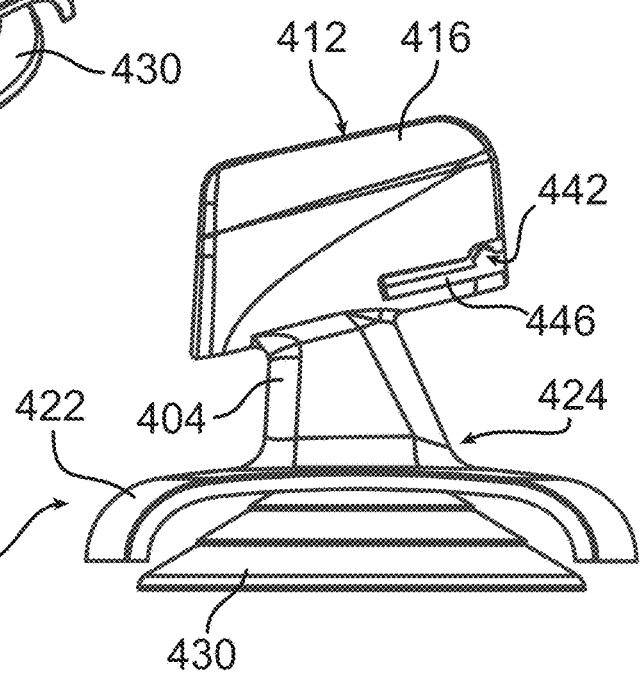
FIG. 21 is a side view of the holder of FIG. 20, which has not been engaged with a supporting surface.
Figure 22:
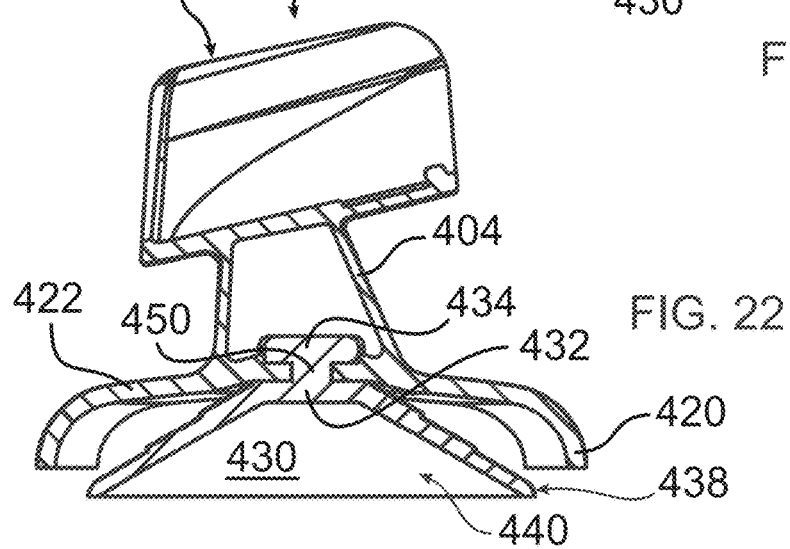
FIG. 22 is a cross-sectional side view of the holder of FIG. 20 taken along line A-A of FIG. 20.

Suction cup 430 is connected at a closed end forming a peak 432 to legs 420, 422, or base extension 404. In the embodiment shown, an attachment button 434 is provided upon a post 450 at peak 432, sized to be inserted through a gap or aperture 436 in base extension 404, whereby suction cup 430 is releasably attached to mounting base 400. Suction cup 430 can be connected by other means, such as adhesive, a removable fastener, crimp, or any other method. Advantageously, however, suction cup 430 can swivel with respect to legs 420, 422, so that suction cup 430 can independently move to form an optimal angular engagement for maintaining a suction or vacuum engagement against a supporting surface. As can be seen in FIGS. 21-22, suction cup 430, in a non-engaged state, extends beyond a furthest extent of legs 420, 422. FIG. 22 illustrates this state in a cross-section taken along line A-A of FIG. 20.

In FIG. 23, mounting base 400 has been pressed against a supporting surface 540, with sufficient force to collapse suction cup 430, and also to bend and collapse legs 420, 422 so that they contact surface 540 and bend further to enable additional evacuation of air from between surface 540 and an interior 440 of suction cup 430. In so doing, legs 420, 422 are spring-loaded, or develop a spring potential which is used to stabilize mounting base 400 as explained further below. FIG. 24 illustrates this state in a cross-section taken along line A-A of FIG. 20.

With reference to FIGS. 25-26, after compressing mounting base 400 to collapse legs 420, 422 and suction cup 430, mounting base 400 may be released, whereupon legs 420, 422 resiliently apply a biasing force to push mounting base in a direction away from surface 540. If surface 540 is sufficiently smooth, and a sealing surface is formed between a peripheral contact surface 438 of suction cup 430, a vacuum is formed within interior 440 of suction cup 530 as button 434 in pulled in a direction away from surface 540. This is achieved as legs resiliently bend to push extension 404 and aperture 436 in a direction away from surface 540 (not shown in FIGS. 24-26). Thus, concomitantly, a suction is formed pulling mounting base 400 in a direction towards surface 540, and legs 420, 422 continue to push against surface 540 in a direction away from surface 540, resulting in a stabilization of base 400 with respect to surface 540.

Legs 420, 422 are cut away along a portion of periphery 448 of suction cup 430, whereby an edge of periphery 448 is exposed. Accordingly, mounting base 400 can be released by lifting a portion of periphery 448 away from surface 540, to admit air into interior 440 to release the vacuum formed therein.

Mounting base 400 can be fabricated of any material, for example metal, wood, plastic, or composite material. Plastic is advantageous as it can be used in a clinical environment, and can be machine washed or wiped with disinfectant cleaners without being damaged. Further, plastic can be selected to be inherently resilient, thereby facilitating the formation of resilient arms 414, 416, resilient detent arm 446, and resilient legs 420, 422. However, other materials can also be used for some or all of mounting base 400, in particular metal, including shape metal alloys, for example. Non-limiting examples include thermoplastics such as Acrylic, ABS, Nylon, PLA, Polybenzimidazole, Polycarbonate, Polyether sulfone, Polyetherether ketone, Polyetherimide, Polyethylene, Polyphenylene oxide, Polyphenylene sulfide, Polypropylene, Polystyrene, Polyvinyl chloride, and Teflon.

Suction cup 430 can be fabricated from any of the foregoing materials which are soft and pliable at room temperature, further including a thermoplastic elastomer, such as Styrenic block copolymers (TPE-s), Thermoplastic olefins (TPE-o), Elastomeric alloys (TPE-v or TPV), Thermoplastic polyurethanes (TPU), Thermoplastic copolyester, Thermoplastic polyamides, and other materials, such as natural or synthetic rubber, or silicone based materials, as understood within the art.

Mounting base 400 can be fabricated using any known method which can produce parts as a unit, as shown, or in portions which can be assembled, for example by gluing, riveting, heat welding, snap fitting, or interference fitting, for example. Parts can be produced by extrusion, grinding, molding, 3D printing, casting, or any other suitable method. A finish can be formed during production, or a coating or painted finish can be applied after production.

Accordingly, the disclosure provides a mounting base system for table or wall mounting of an instrument of the disclosure. The mounting base 400 includes elastomeric suction cup 430 mounted to a semi rigid mounting base 400. The suction cup has a center post 450 that is connected to the center of the base 400, creating a two-part assembly which provides the suction cup 430 with the ability to flex laterally and to be flattened upon a mounting surface.

In use, mounting base 400 together with suction cup 430 are pressed firmly downward against the surface 540 upon which base 400 is to be mounted, by the user (FIGS. 23-24). In the process of this action the suction cup 430 flattens and displaces air beneath it, and the flexible legs 420, 422 on the semi-rigid base 400 flex as base 400 and suction cup 430 are moved downwards, suction cup 430 being moved downward via its connection at center post 450, button 434, and contact with peak 432 and an underside of base extension 404. When downward pressure is removed and the suction cup is fully flattened, there is an inherent relaxing upward of suction cup 430, pushing upwards upon center post 450 and peak 432. To limit the upward movement of suction cup 430, which might otherwise lift legs 420, 422 free of surface 540, arms 420, 422 flex and act as a spring, both pressing downward against the table surface and pushing upward away from surface 540 against button 434. This spring action results in an overall tightening of base 400 relative to mounting surface 540 to create a stable and secure attachment to mounting surface 540.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. An assembly including:
   a therapeutic tool for carrying out a therapeutic procedure; and
   a device for vibrating body tissue of a body part, the device comprising:
   a frame;
   an activatable source of vibration connected to the frame; and
   a removable tip connectable to the frame and having a distal end, the tip connected to the source of vibration when the tip is connected to the frame, so as to vibrate the distal end when the source of vibration is activated, the distal end forming
   mutually facing arms which define an opening between the arms,
   each arm forming a projection extending at an angle from the arm, the projections shaped to fit the body part, the arms and projections sized and dimensioned to position, retain, and transmit vibration to the body part in a position proximate the opening,
   wherein the arms of the device are shaped to surround and mateably contact a tool end of the therapeutic tool inserted into the opening between the arms of the device, so as to help maintain a position of the tool end.

2. The assembly of claim 1, wherein the arms are sized, dimensioned, and positioned to surround a portion of a pad of a finger when the projections are positioned against an end of the finger.

3. The assembly of claim 1, wherein the projections have a sloped surface corresponding to the curved surface at the end of the finger.

4. The assembly of claim 1, the projection forming a sloped surface corresponding to the end of a finger.

5. The assembly of claim 4, wherein the sloped surface is formed at least in part by a resilient overmolded portion formed over the arms.

6. The assembly of claim 1,
   wherein the arms of the device are resiliently connected to the tip, and
   when the arms of the device surround and mateably contact the tool end of the therapeutic tool, the arms of the device resiliently grip the tool end to help maintain its position during use of the tool.

7. The assembly of claim 6, wherein the arms and the projections of the device are sized and dimensioned to retain both the body part in position, and to grip the tool end of the therapeutic tool, at the same time.

8. The assembly of claim 1, further including an electromagnetic tag positioned upon the removable tip, and an electromagnetic reader antenna positionable proximate the tag when the removable tip is installed upon the frame.

9. The assembly of claim 1, wherein the arms of the device are shaped to surround almost entirely and positively position the tool end of the therapeutic tool during use of the tool.

10. The assembly of claim 1, wherein the arms of the device resiliently apply a force to the tool end so as to resiliently grip the tool end to help maintain its position during use of the tool.

11. The assembly of claim 1, wherein the tool end is shaped to match the shape of the opening between the arms of the device.

12. The assembly of claim 11, wherein the tool end has a tapered round end shape.

13. An assembly including:
   a device for vibrating body tissue of a body part, the device comprising:
   a main frame;
   an activatable source of vibration connected to the main frame; and
   a removable tip connectable to the main frame and having a distal end, the tip connected to the source of vibration when the tip is connected to the main frame, so as to vibrate the distal end when the source of vibration is activated, the distal end forming
   mutually facing arms which define an opening between the arms,
   each arm forming a projection extending at an angle from the arm, the projections shaped to fit the body part, the arms and projections sized and dimensioned to position, retain, and transmit vibration to the body part in a position proximate the opening, and
   a mounting base for supporting the device upon a surface, the mounting base comprising:
   a suction cup having an open end and a closed end;

a flexible frame connected to the suction cup proximate the closed end,
  the flexible frame bendable to enable the suction cup to be compressed against the surface to expel air from within the suction cup, and
  when the suction cup is not being compressed and is in suction contact with the surface, the flexible frame itself resiliently applying a biasing force to push the flexible frame in a direction away from the surface; and
a holder sized to be connected to the flexible frame and dimensioned to hold the device when the device is inserted into the holder.

14. The assembly of claim 13, wherein the flexible frame includes at least two flexible support legs.

15. The assembly of claim 14, wherein the support legs resiliently apply the biasing force to push the flexible frame in the direction away from surface.

16. The assembly of claim 14, wherein the support legs are shaped so that a bottom of each of the support legs rests upon the surface when the mounting base is connected to the surface using the suction cup.

17. The assembly of claim 14, wherein when the mounting base is connected to the surface using the suction cup, the suction cup pulls the flexible frame in a direction toward the surface while the support legs of the flexible frame push against the surface in the direction away from surface so as to a stabilize the mounting base with respect to the surface.

18. The assembly of claim 14, wherein when the flexible frame is pressed toward the surface, the suction cup is compressed against the surface while the support legs bend so as to contact the surface and also enable additional evacuation of air from between the surface and an interior of the suction cup.

19. The assembly of claim 14, wherein when the mounting base is connected to the surface using the suction cup, the support legs flex so as to both press downward against the surface and push upward away from surface so as to tighten the mounting base relative to the surface.

20. The assembly of claim 13, wherein the flexible frame is fabricated from resilient plastic.

21. The assembly of claim 13, wherein the suction cup includes a post at the closed end, the post connected to the flexible frame to enable the suction cup to move with respect to the flexible frame.

22. The assembly of claim 13, wherein the holder includes two opposed flexible arms sized to hold the device therebetween.

23. The assembly of claim 13,
  wherein the holder includes at least one of a resiliently mounted projection or aperture and the device includes the other thereof, and
  wherein the resiliently mounted projection and aperture mate when the device is positioned within the holder, to thereby maintain a predetermined position of the device within the holder.

24. The assembly of claim 13, wherein the holder is connected to the flexible frame at a non-orthogonal angle with respect to the surface when the mounting base is connected to the surface using the suction cup.

25. The assembly of claim 13, wherein the flexible frame is shaped so that its bottom is in contact with the surface when the mounting base is connected to the surface using the suction cup.

* * * * *